United States Patent
Zou et al.

(10) Patent No.: US 8,437,522 B2
(45) Date of Patent: May 7, 2013

(54) MOTION INDEX FOR MEDICAL IMAGING DATA BASED UPON GRANGEAT'S FORMULA

(75) Inventors: Yu Zou, Naperville, IL (US); Ilmar Hein, Chicago, IL (US)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 276 days.

(21) Appl. No.: 13/029,318

(22) Filed: Feb. 17, 2011

(65) Prior Publication Data
US 2012/0213414 A1 Aug. 23, 2012

(51) Int. Cl.
*G06K 9/00* (2006.01)

(52) U.S. Cl.
USPC .......................................................... 382/128

(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS 5,124,914 A 6/1992 Grangeat

OTHER PUBLICATIONS

Extended European Search Report dated Jun. 18, 2012 for corresponding EP Application No. 12155921.5.
Hengyong, Yu et al., "Data Consistency Based on Rigid Motion Artifact Reduction in Fan-Beam CT", IEEE Transactions on Medical Imaging, IEEE Service Center, Piscataway, NJ, US, vol. 26, No. 2, Feb. 1, 2007, pp. 249-260.
Kachelriess, Marc et al., "Kymogram detection and kymogram-correlated image reconstruction from subsecond spiral computed tomography scans of the heart", Medical Physics, AIP, Melville, NY, US, vol. 29, No. 7, Jul. 1, 2002, pp. 1489-1503.
J. Vander Sloten, P. Verdonck, M. Nyssen, J. Haueisen (Eds.): ECIFMBE 2008, IFMBE Proceedings 22, pp. 505-508, 2008.

*Primary Examiner* — Atiba O Fitzpatrick
(74) *Attorney, Agent, or Firm* — Yoshida & Associates, LLC

(57) ABSTRACT

Embodiments and processes of computer tomography perform tasks associated with selecting a portion of projection or emission data that contain the least amount of motion based upon a predetermined motion index, a derivative of plane integral (DPI). Other embodiments and processes of computer tomography perform tasks associated with determining an amount of direction-dependent motion in an object based upon a comparison of the DPIs in predetermined directions.

34 Claims, 12 Drawing Sheets

110R

205

MOTION INDEX FOR MEDICAL IMAGING DATA BASED UPON GRANGEAT'S FORMULA

FIELD

Embodiments described herein generally relate to a motion index in X-ray Computed Tomography (CT), Positron Emission Tomography (PET) and Single Photon Emission Computed Tomography (SPECT) imaging systems and methods.

BACKGROUND

In general, medical imaging data generally assumes a stationary object. That is, it is assumed that the data has been acquired while a patient makes no motion. The motion includes both body movements and organ movements during the data acquisition. When the images are reconstructed based upon acquired data reflecting some motion, the reconstructed images substantially suffer from motion artifacts so that these images could lead the doctors to an inaccurate diagnosis.

One approach in improving the image quality is to identify certain portions of the acquired data that reflect the least amount of motion. Since the identified portions of the data have the least amount of motion, when the images are reconstructed from the projection data with the least motion, the reconstructed images are also least affected by the motion artifacts. This approach utilizes a motion index to identify certain data portions that had been acquired while the least amount of motion took place.

Some prior art motion indexes are based upon the Helgason-Ludwig consistency condition, complementary rays and a sinogram. Unfortunately, the prior art techniques are either inapplicable to different situations or inaccurate over various projection data sets. Thus, a new motion index remains to be desired for various applications and projection data sets.

A new motion index will be introduced for identifying a certain portion of data that has been acquired with a minimal amount of motion. Image reconstruction is implemented based upon the above identified data for substantially reducing motion artifacts in the reconstructed images in the hope that these improved images could prevent the doctors from making an inaccurate diagnosis.

DETAILED DESCRIPTION

One approach in improving the image reconstruction is to identify portions of the data involving the least amount of motion. For example, one approach is to identify certain portions of projection data that had been acquired while the least amount of motion took place in the region of interest. Since the identified portions of projection data have the least amount of motion, when the images are reconstructed from the selected projection data with the least motion, the reconstructed images are likely to be least affected by the motion artifacts. In other words, this approach utilizes the consistent portion of the projection data. By the same token, a similar reconstruction approach is to utilize the projection data that are centered on the above described consistent range of data. In either case, the above identified projection data substantially reduces motion artifacts in the reconstructed images.

Figure 1:
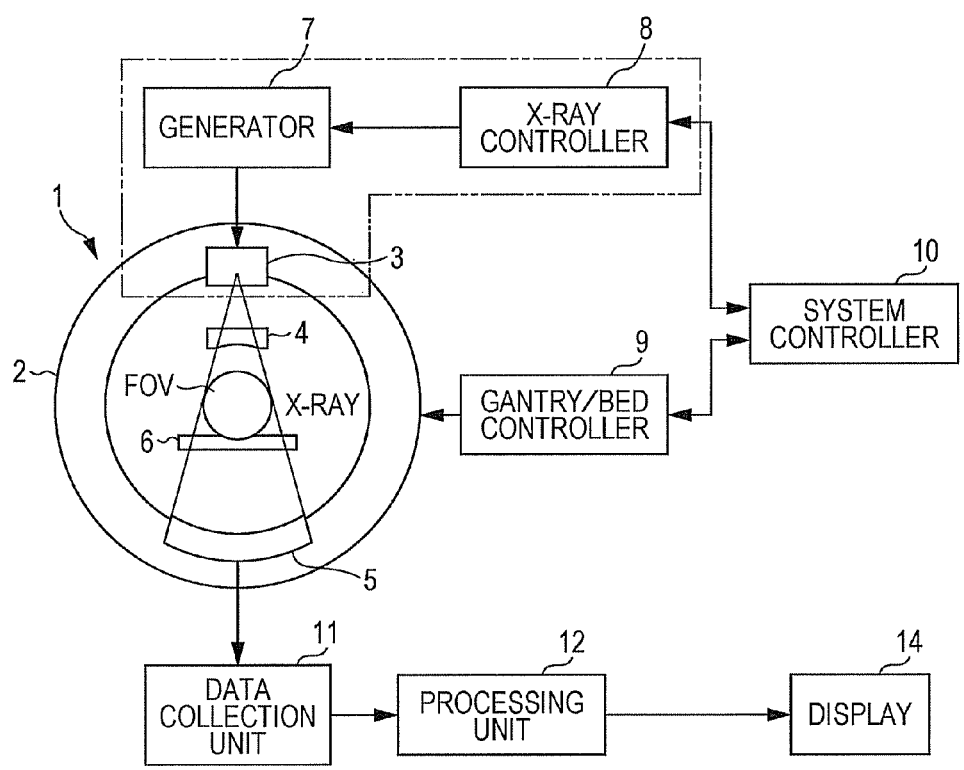
FIG. 1 is a diagram illustrating one embodiment of an x-ray computed topographic imaging system according to the present invention.

FIG. 1 is a diagram illustrating one embodiment of an x-ray computed topographic imaging system according to the present invention. The projection data measurement system includes a gantry 1, which accommodates an x-ray source 3 and a two-dimensional array type x-ray detector 5. The x-ray source 3 and the two-dimensional array type x-ray detector 5 are installed on a rotating ring 2 at opposite sides of a subject, who is laid on a sliding sheet bed 6. The rotating ring 2 rotates around a predetermined rotational axis while the sliding bed 6 moves along the rotational axis at a predetermined speed. A gantry/bed controller 9 synchronously controls the revolution of the rotating ring. 2 and the sliding movement of the sliding bed 6. In the following embodiments, projection data is collected while the x-ray source 3 travels either a helical path in a helical scanning mode or a circular path in a circular scanning mode.

The x-ray source 3 optionally emits a cone-beam or approximately cone-shaped x-ray flux that is directed onto the subject through an x-ray filter 4. An x-ray controller 8 supplies a trigger signal to a high voltage generator 7, which applies high voltage to the x-ray source 3 upon receiving the trigger signal. Furthermore, a system controller 10 exerts an overall control over both the x-ray controller 8 and the gantry/bed controller 9 so that x-rays are emitted continuously or intermittently at fixed angular intervals from the x-ray source 3 while the rotating ring 2 and the sliding bed 6 are respectively in predetermined rotation and motion.

X-rays that have passed through the subject are detected as electrical signals or raw data by the two-dimensional array type x-ray detector 5. In the x-ray detector 5, a plurality of detector elements are arranged in one dimensional row, and a plurality of the rows is stacked to construct a two-dimensional array. In certain situation, each detector element corresponds with one channel. A data collection unit 11 amplifies the output signal from the two-dimensional array type x-ray detector 5 for each channel and converts to a digital signal so as to produce projection data.

A processing unit 12 subsequently perfoinis various processing tasks upon the projection data that has been delivered from the data collection unit 11. For example, the processing unit 12 performs on the projection data desired operation including but not limited to data sampling and shifting, filtering, selection, backprojection and reconstruction.

The processing unit 12 determines backprojection data based upon the projection data. In a circular scanning system using a cone-beam of x-rays, the imaging region (effective field of view) is of cylindrical shape of radius R centered on the axis of revolution. The processing unit 12 defines a plurality of voxels (three-dimensional pixels) in this imaging region and finds the backprojection data for each voxel. The three-dimensional image data or tomographic image data is compiled based upon the backprojection data, and a display device 14 displays a three-dimensional image or tomographic image according to the three-dimensional image data.

As will be later described in details, the processing unit 12 also performs tasks related to selecting a certain portion of the projection data before backprojection and reconstruction. In certain embodiments, the processing unit 12 selects before backprojection and reconstruction a portion or portions of the projection data experiencing the least amount of motion according to a predetermined motion index. The projection data selection is an important task for improving an image of non-stationary organs such as the heart and lungs according to the current invention.

As well known, an object or patient attenuates the x-ray photon beam (ray), and the attenuated intensity I at the detector element k is defined in Equation (1) as follows:

$$I_k = I_k^0 \exp(-\int_l \mu(x) dx) \quad (1)$$

where $\mu(x)$ is the attenuation function to be reconstructed, $I_k^0$ is the beam intensity before attenuation by $\mu(x)$ as originally produced by the x-ray tube but after penetrating through the x-ray (wedge, bowtie) filter, and $\int_l \mu(x) dx$ is the line integral of $\mu(x)$ along the line l. Mathematically, $\mu(x)$ can be reconstructed given a set of line integrals corresponding to a plurality of the lines l. Therefore, measured intensity data are to be converted into line integrals as follows in Equation (2):

$$\int_l \mu(x) dx = \ln(I_k^0) - \ln(I_k) \quad (2)$$

X-ray tomographic imaging consists of the following three main steps, data acquisition, data processing and data reconstruction. In data acquisition, the x-ray intensity data are collected at each detector element of the detector 5 and at each predefined angular view position $\beta$ while the gantry 1 is rotated. The detector 5 measures incident x-ray flux by integrating energy (charge) or counting photons, and the measured signal is converted into an electric signal. Then, the electric signal is transferred from a rotating part of the gantry 1 to a stationary part though the rotating ring 2.

In data processing, data is converted from x-ray intensity measurements to the signal corresponding to line integrals according to Equation (2). Also, various corrections steps are applied to reduce undesirable effects of physical phenomena such as scatter and x-ray beam hardening to compensate the non-uniform response function of each detector element, and also to reduce noise.

In the present invention, the processing unit 12 of FIG. 1 performs data selection as illustrated in the following embodiments. In some embodiments or processes, data selection is related to motion alone. Motion is determined by certain predetermined indexes such as the derivative of plane integrals (DPI). These embodiments and processes are merely exemplary and are optionally implemented in a variety of different ways.

In clinical applications, two major types of motion include motion of the heart (cardiac motion) and lung motion. Cardiac data is generally obtained over several heart beats at a slow helical pitch so that redundant data are sufficiently available for gated reconstruction. During the data acquisition, electrocardiogram (ECG) is also obtained for information on cardiac motion.

Still in relation to selecting certain portion of the projection data based upon motion, lung data is acquired in the following manner. In general, lung data is collected at a faster helical pitch so that some redundant data is available, but it is not usually enough for gated reconstruction. In some cases, lung data may be sufficient only for a very limited gated reconstruction. Unlike ECG for the cardiac motion, no external motion information is generally available for reconstruction with respect to lung data. In addition to the above described type of the clinical data, motion may be caused by the movement of a patient during the data acquisition. This body motion may be in combination with the organic movement.

In both cardiac and lung cases, available redundant data is selected based on object motion. The main idea is to use a predetermined motion index such as DPI so that consistent data portion is selected. In the following disclosure on the exemplary embodiments, a processing unit or its equivalent device performs tasks related to the determination of motion index values for the projection data and the above described selection of the consistent portion(s) of the projection data based upon the predetermined motion index values. By the same token, in the following disclosure on exemplary processes or methods, a processing step is used to generally include steps or sub steps that are related to the above described determination and selection functions.

To understand the motion index as used in the embodiments according to the current invention, the following relationship is explained among line integrals, plane integrals and the derivative of plane integrals (DPI). A 3D cone beam projection of an image function $f(\vec{x})$ can be written as Equation (3) below:

$$g(\vec{a}(\lambda), \hat{\beta}) = \int_0^\infty f(\vec{a}(\lambda) + r\hat{\beta}) dr \quad (3)$$

where $g(\vec{a}(\lambda), \hat{\beta})$ is projection or line integral, $\vec{a}(\lambda)$ represents the source position and $\hat{\beta} = \vec{e}(\alpha, \gamma)$ indicates a unit vector in 3D image space determined by the source position $\vec{a}(\lambda)$ and cone angle $\alpha$ and fan angle $\gamma$ or $\hat{\beta}$. r is a distance parameter from a source to a point in the object.

Planar integral is defined in Equation (4) below:

$$p(l, \hat{n}) = \int_{R^3} f(\vec{x}) \delta(l - \vec{x} \cdot \hat{n}) d\vec{x} \quad (4)$$

where $\hat{n}$ is the normal of the plane and l is the distance from the origin to the plane.

To derive Grangeat's formula, consider the following:

$$\int_{S^2} g(\vec{a}(\lambda), \hat{\beta}) \delta'(\hat{\beta} \cdot \hat{n}) d\hat{\beta} = \int_{S^2} d\hat{\beta} \int_0^\infty f(\vec{a}(\lambda) + r\hat{\beta}) dr \delta'(\hat{\beta} \cdot \hat{n}) \quad (5)$$

To have the right hand-side of Equation (5), $g(\vec{a}(\lambda), \hat{\beta})$ of Equation (5) is substituted by the right-hand side of Equation (3). Furthermore, $\vec{x} = \vec{a} + r\hat{\beta}$ is assumed to have Equation (6) below.

$$= \int_{S^2} d\hat{\beta} \int_0^\infty r^2 dr f(\vec{x}) \frac{1}{r^2} \delta'\left(\frac{1}{r}(\vec{x} - \bar{a}(\lambda)) \cdot \hat{n}\right) \quad (6)$$

From Equation (4), by cancelling r's, Equation (7) is obtained as below:

$$= \int_{R^3} d\vec{x} f(\vec{x}) \delta'((\vec{x} - \vec{a}(\lambda)) \cdot \hat{n}) \quad (7)$$

On the other hand, by differentiating Equation (4), Equation (8) is obtained below as the derivative of plane integrals (DPI):

$$\frac{\partial p(l, \hat{n})}{\partial l} = \int_{R^3} f(\vec{x}) \delta'(l - \vec{x} \cdot \hat{n}) d\vec{x} = -\int_{R^3} f(\vec{x}) \delta'(\vec{x} \cdot \hat{n} - l) d\vec{x} \quad (8)$$

By comparing Equations (7) and (8) and assuming that the condition $\vec{a}(\lambda) \cdot \hat{n} = l$ is true, Grangeat's formula in Equation (9) is derived as below: According to Grangeat's formula, the derivative of plane integrals (DPI) is related to the cone beam projection data as expressed in Equation (5):

$$\frac{\partial p(l, \hat{n})}{\partial l}\bigg|_{l=\vec{a}(\lambda) \cdot \hat{n}} = -\int_{S^2} g(\vec{a}(\lambda), \hat{\beta}) \delta'(\hat{\beta} \cdot \hat{n}) d\hat{\beta} \quad (9)$$

$g(\vec{a}(\lambda), \hat{\beta})$ is projection or line integral, $\vec{a}(\lambda)$ represents the source position and $\hat{\beta} = \vec{e}(\alpha, \gamma)$ indicates a unit vector in 3D image space determined by the source position $\vec{a}(\lambda)$ and cone angle $\alpha$ and fan angle $\gamma$ or $\hat{\beta}$. Thus, Equation (9) can be also written as Equation (10) below:

$$\frac{\partial p(l, \hat{n})}{\partial l}\bigg|_{l=\vec{a}(\lambda) \cdot \hat{n}} = -\int_{S^2} g(\lambda, \alpha, \gamma) \delta'(\hat{n} \cdot \hat{e}(\alpha, \gamma)) d\hat{e}(\alpha, \gamma) \quad (10)$$

As expressed in Equation (10), the DPI is determined from projection data in various views, and the determined DPI values are the same if the data are consistent. This is because the planar integral is dependent only on image function $f(\vec{x})$. DPI has the same feature. In CT imaging, it is assumed that the object is stationary and the image function is is the same during a scan. Therefore, DPI is unique on a plane for a specific image function (object). It is not dependent on how and where the DPI is obtained (i.e., through line integrals at different locations). The difference in DPI on the same plane from different x-ray source points necessarily indicates a change in the image function during the scan (i.e., moving of the source point). In other words, the DPI values are the same if there is no motion in the projection data.

To use the above feature of DPI as a motion index, embodiments of the current invention are implemented in various ways. In one embodiment, the DPI values in two neighboring views are compared as a motion index to examine the consistency. The temporal resolution is determined by the scan time of two views. However, due to aliasing and noise, the comparison may not be reliable for the two immediately neighboring views. For this reason, in another embodiment, a running average of DPI's over a predetermined number of views such as 63 consecutive views is used to determine an amount of motion in order to reduce undesirable effects of aliasing error and noise.

The temporal resolution substantially improves in detecting a sudden or quick movement when DPI's are used as a motion index. Other motion indexes such as complementary views require that the two corresponding projection data sets are acquired about 180 degrees apart. During the source travelling over the 180 degrees, the object such as the heart may experience certain small reciprocating movements. In other words, by the time when the source completes its travels over the 180 degrees, a certain part of an object moves to a destination and comes back to the original position. Thus, a time lag in acquiring the projection data causes a failure in capturing certain fast motion in the object.

Figure 2:
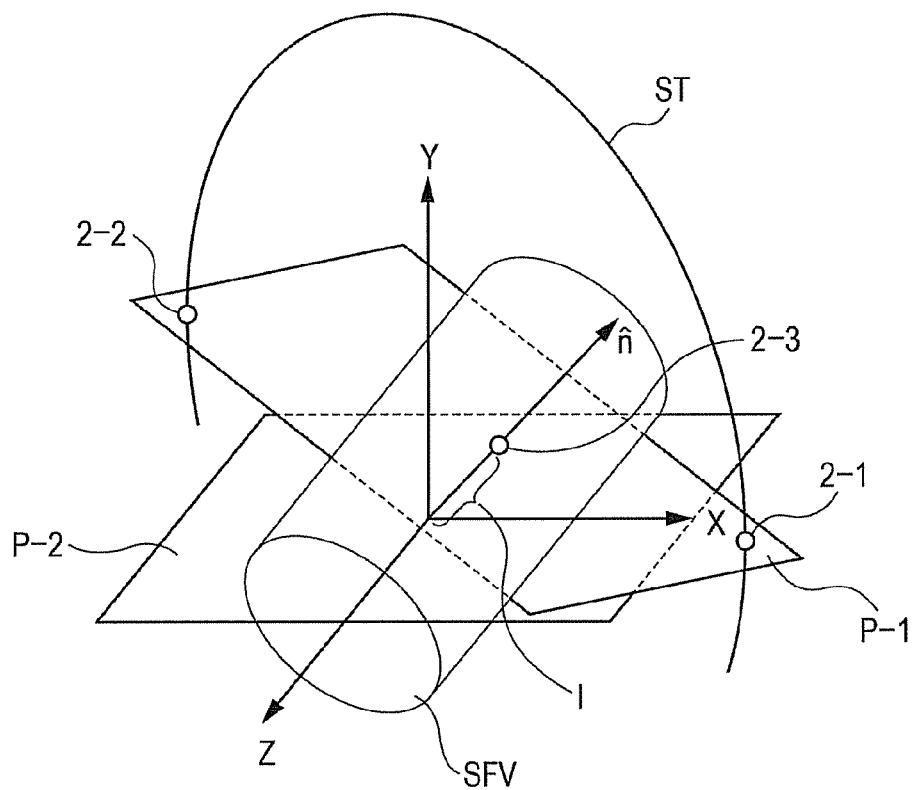
FIG. 2 is a diagram illustrating a cone-beam system for and a method of determining a motion index according to the invention.

Now referring to FIG. 2, a diagram illustrates a cone-beam system for and a method of determining a motion index according to the invention. The motion index is used for selecting consistent portions of projection data. In general, conebeam X-rays are emitted from an X-ray source that travels along a predetermined source trajectory ST. At each of a projection angle β with respect to the x axis, the x-rays are emitted with a cone angle α and angle α and a fan angle γ and pass through an object with a scanned field of view (SFV). Thus, the projection data are acquired in the above described manner.

Still referring to the diagram in FIG. 2, a plane P-1 is a test plane and includes a point 2-3. The test plane P-1 is perpendicular to a unit vector n̂, which intersects the test plane P-1 at a distance l from the origin of the axes X, Y and Z. A plane P-2 is located on the X and Z axes. Assuming a 3D source trajectory ST, two points 2-1 and 2-2 are on the source trajectory ST and are on the test plane P-1. That is, projection data for each view is available from the two points 2-1 and 2-2. For the test plane P-1, the derivatives of plane integrals (DPI) are obtained from the cone beam projection data at the two points 2-1 and 2-2. The DPI from the point 2-1 is equal to the DPI from the point 2-2 if the projection data at the two points 2-1 and 2-2 are consistent (i.e. no motion). In fact, the difference in the two DPI values represents the inconsistency of the projection data from the two views. Assuming that the inconsistency is primarily caused by motion, the difference in the two DPI values defines an amount of motion and is used as a motion index.

In the above described determination of the motion index, the two points 2-1 and 2-2 are 180 degrees apart. Since the point 2-1 must travel along the source trajectory ST to reach the point 2-2 over a half rotation of the gantry, the associated projection data at the two points 2-1 and 2-2 have a corresponding amount of relatively long time difference. In other words, the projection data at the two points 2-1 and 2-2 do not have an optimal temporal resolution.

Figure 3:
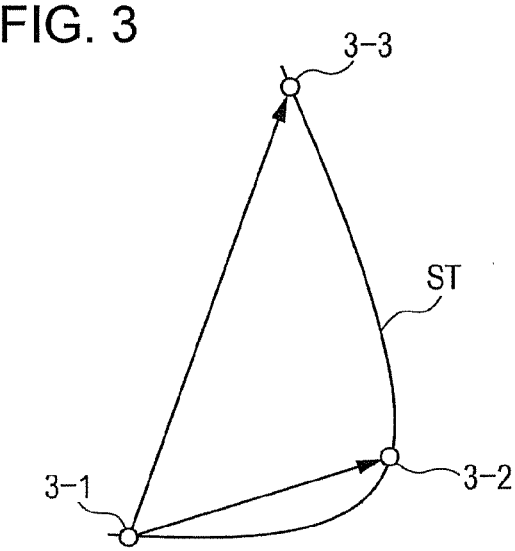
FIG. 3 is a diagram illustrating three points on a predetermined source trajectory in determining a motion map according to the current invention.

Now referring to FIG. 3, a diagram illustrates three points on a predetermined source trajectory in determining a motion map according to the current invention. Assuming a 3D source trajectory ST, three points 3-1, 3-2 and 3-3 on the trajectory ST decide a plane. As already described above with respect to Equations (3) through (11), the derivatives of the planar integrals (DPI) are related to the line integrals according to Grangeat's formula. Based upon the three source points 3-1, 3-2 and 3-3 on the plane, the DPI is determined three times. In general, if the projection data at the three source points 3-1, 3-2 and 3-3 were consistent, the three DPI values would be identical. On the other hand, if the data were not consistent, the difference in DPI values would measure the data inconsistency or an amount of motion.

Assuming that the data inconsistency is due to motion, one exemplary motion map M is defined by Equation (11) below:

$$M(\lambda_1, \lambda_2) = \frac{1}{\lambda_3 - \lambda_1} \int_{\lambda_1}^{\lambda_3} \left[ \left| \frac{\partial p(l, \hat{n})}{\partial l} \bigg|_{l=\vec{a}(\lambda_1)} - \frac{\partial p(l, \hat{n})}{\partial l} \bigg|_{l=\vec{a}(\lambda_2)} \right| \right.$$
$$\left. + \left| \frac{\partial p(l, \hat{n})}{\partial l} \bigg|_{l=\vec{a}(\lambda_3)} - \frac{\partial p(l, \hat{n})}{\partial l} \bigg|_{l=\vec{a}(\lambda_2)} \right| \right] d\lambda_2 \quad (11)$$

where $M(\lambda_1,\lambda_3)$ indicates the difference in DPI among the three points 3-1, 3-2 and 3-3. That is, the difference in DPI between the two points 3-1 and 3-3 is determined based upon the sum of DPI difference between the two points 3-1 and 3-2 and DPI difference between the two points 3-2 and 3-3. If the two DPI differences were each zero, the sum of the two DPI difference would be also zero, indicating that the projection data is consistent. On the other hand, if either or both of the two DPI differences were not zero, the sum of the two DPI difference would be also non-zero, indicating that the projection data is inconsistent.

Figure 4:
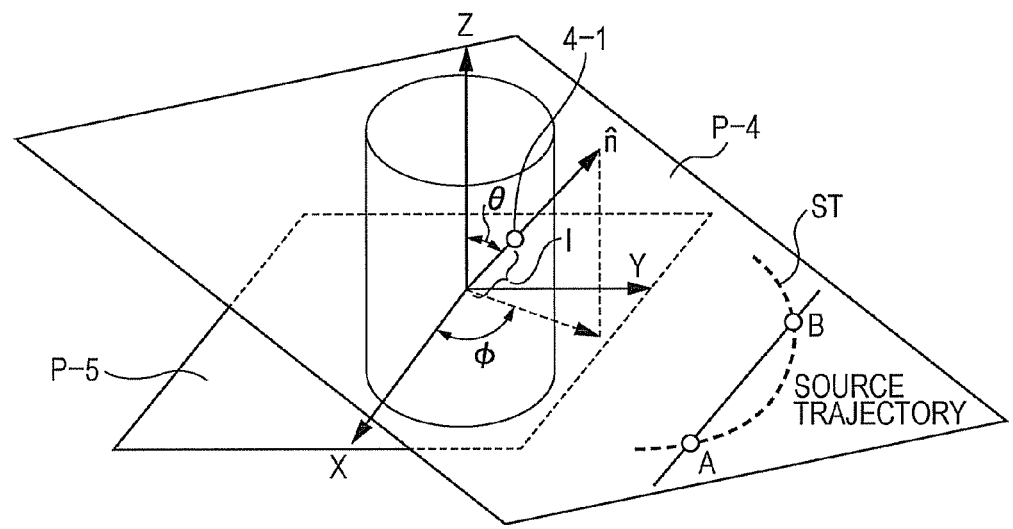
FIG. 4 is a diagram illustrating a cone-beam system for and a method of determining a motion index according to the invention.

Now referring to FIG. 4, a diagram illustrates a cone-beam system for and a method of determining a motion index according to the invention. The motion index is used for selecting consistent portions of projection data. In general, conebeam X-rays are emitted from the X-ray source that travels along a predetermined source trajectory ST. At each projection view, the x-rays are emitted with a cone angle α and a fan angle γ and pass through an object with a scanned field of view (SFV). Thus, the projection data are acquired in the above described manner.

Still referring to the diagram in FIG. 4, a plane P-4 is a test plane and includes a point 4-1. The test plane P-4 is perpendicular to a unit vector n̂, which intersects the test plane P-4 at angles φ and θ with a distance l from the origin of the axes X, Y and Z. A plane P-5 is located on the X and Z axes. Assuming a 3D source trajectory ST, two points A and B are on the source trajectory ST and also on the test plane P-4. That is, any two points A and B on the trajectory ST define a family of planes that are also referred to as test planes. Although a single test plane P-4 is only illustrated in FIG. 4, there is in fact a family of test planes. In other words, for each test plane, the derivative of plane integrals (DPI) is determined from the cone beam projection data at point A and point B. The DPI from the point A is equal to the DPI from the point B if the projection data at the two points A and B are consistent (i.e. no motion). In fact, the difference in the two DPI values represents the inconsistency of the projection data from the two views. Assuming that the inconsistency is primarily caused by motion, the difference in the two DPI values defines an amount of motion and is used as a motion index.

In the above described determination of the motion index, the two points A and B are sufficiently close so that they are a fraction of 180 degrees apart. Since the point A travels over a short distance on the source trajectory ST to reach the point B, the associated projection data at the two points A and B have a corresponding amount of short time difference. In other words, the projection data at the two points A and B have a sufficiently optimal temporal resolution.

Figure 5:
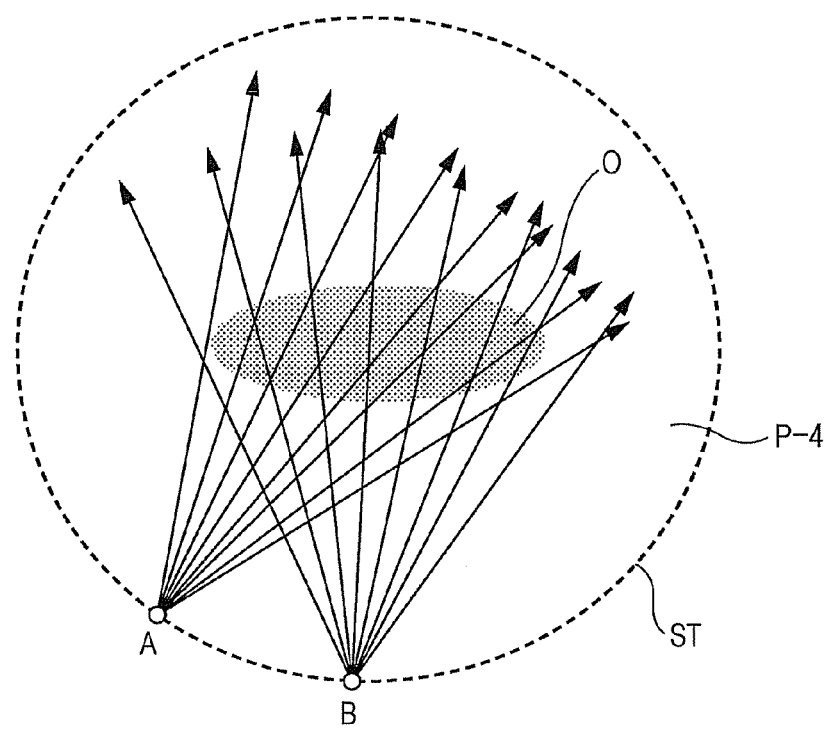
FIG. 5 is a diagram illustrating a cone-beam system for and a method of determining a motion index according to the invention.

Now referring to FIG. 5, a diagram illustrates a cone-beam system for and a method of determining a motion index according to the invention. The motion index is used for selecting consistent portions of projection data. In the illustrated example, conebeam X-rays are emitted from the X-ray source that travels along a predetermined circular source trajectory ST. As described with respect to FIG. 4, at each projection view, the x-rays are emitted with a cone angle α and a fan angle γ and pass through an object O. Although these angles are not shown in FIG. 5, the projection data are acquired in the above described manner.

Still referring to the diagram in FIG. 5, a plane P-4 is a middle plane that is a plane that contains the circular source trajectory ST along points A and B. Assuming a cone beam scan with a circular trajectory, the middle plane is taken as the test plane from a family of other planes. The DPI in the middle plane is obtained from the projection data near the middle plane. To calculate the derivative, at lease two row data are required in each view. The DPI from each view would be identical if the projections were consistent. On the other hand, the variation in the DPI would exist if the projections were inconsistent. In any case, the temporal resolution for any quick or subtle movement is accurately detected using DPI's without involving too much calculation. This is because the two source locations are at any angle with each other in determining a difference between the two DPI's. That is, Δt (time for the source to move from the first location to the second location) can be made as small as the two adjacent source views. In addition, test planes are flexibly selected. From Equation (10), the DPI on the middle plane for the circular trajectory is determined by the following Equation (12). This is because, the cone angle α is assumed to be 0 for the middle plane.

$$\frac{\partial p(l, \hat{n})}{\partial l} \bigg|_{l=\vec{a}(\lambda)\cdot\hat{n}} = \int_0^{2\pi} \frac{\partial g(\lambda, \alpha, \gamma)}{\partial \alpha} \bigg|_{\alpha=0} d\gamma \quad (12)$$

In relation to FIG. 5, a family of other planes may be utilized to analyze complex movements based upon the DPI's associated with the family of planes. For example, cardiac movements are not uniform in all directions. When a plurality of the planes are used as test planes for certain non-uniform cardiac movements, a set of the DPI's associated with a first combination of planes may indicate some movement in certain directions while the same DPI's associated with a second combination of planes may not indicate any movement in certain other directions. In other words, the DPI's are used to implement a technique to analyze direction-dependent movements.

Figure 6:
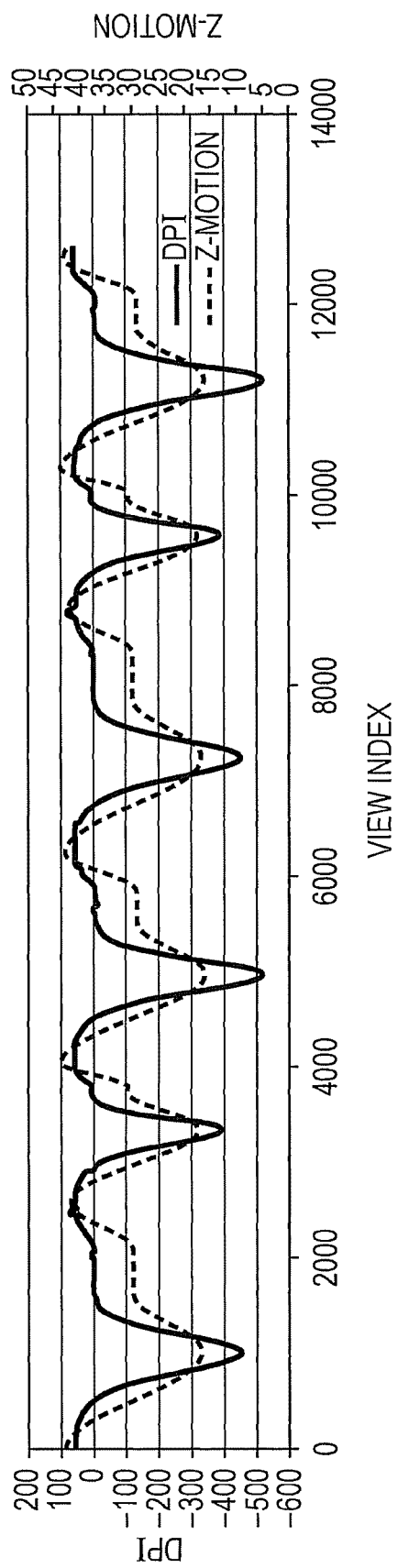
FIG. 6 illustrates a numerical simulation to show the accuracy and temporal resolution of the motion index.
Figure 7A:
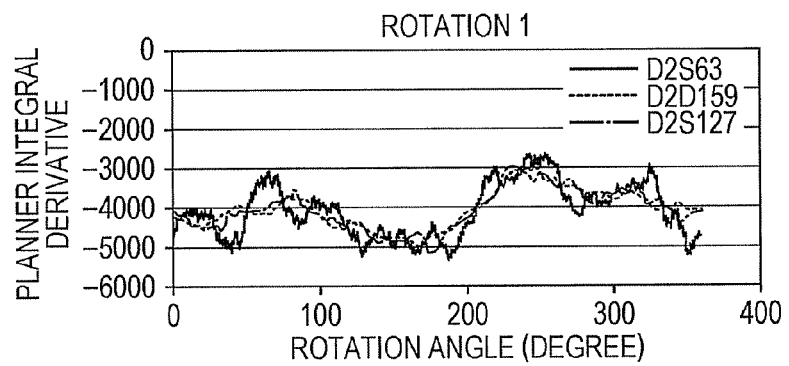
FIGS. 7A through 7D show the planar integral derivatives or derivative of planar integral (DPI's) during four consecutive rotations over a circular trajectory in a clinical cardiac scan.
Figure 7B:
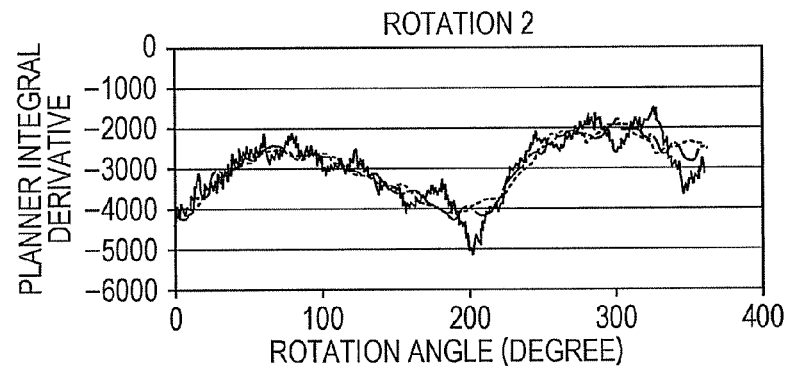
Figure 7C:
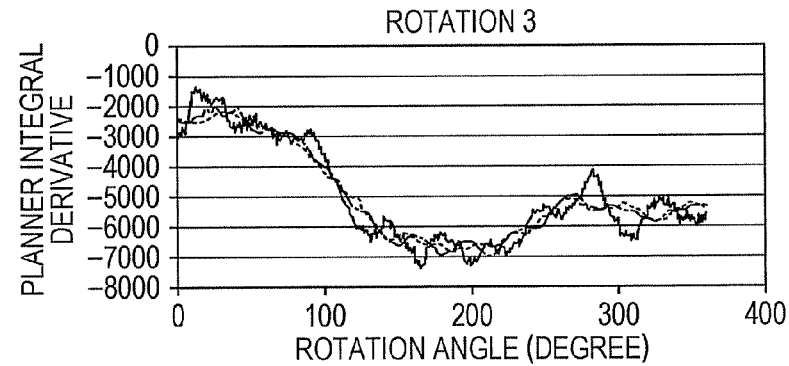
Figure 7D:
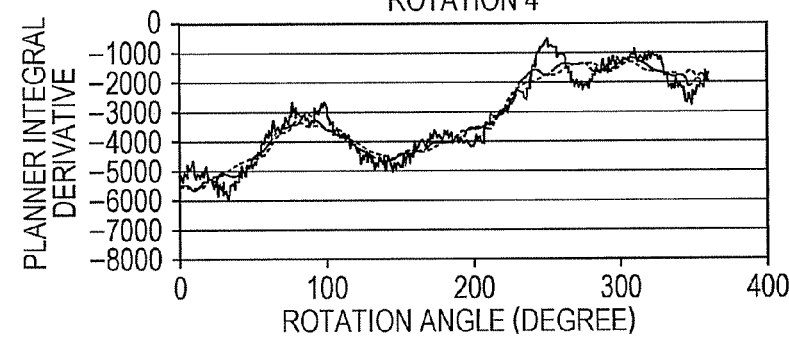

Now referring to FIG. 6, a numerical simulation is utilized to show the accuracy and temporal resolution of motion index—DPI. The simulation of a beating heart is based upon a beating hollow ellipsoid having 30 mm resting outer wall and 25 mm inner wall in diameter. The center of the ellipsoid is placed at a fixed z position while the x- and z-dimensions of the ellipsoid expand and contract with time to simulate the beating heart. In heart. In order to confirm the effectiveness of the DPI motion index for the cardiac motion, the simulated heart expanded and contracted in an irregular manner from beat to beat by varying period and amplitude. As shown in FIG. 6, the DPI is indicated by a solid line while the z-motion is indicated by a dotted line. The cardiac motion phases as indicated in the z-motion substantially correspond to the DPI curve for each heart beat. In other words, the DPI motion index substantially reflects various patterns in cardiac motion.

FIGS. 7A through 7D show the planar integral derivatives or derivative of planar integral (DPI's) during four consecutive rotations over a circular trajectory in a clinical cardiac scan. For each rotation, the DPI's are averaged with three widths of 63, 127, and 159. It appears that two peaks near 90 degrees and 300 degrees are attributed to beam hardening, which could be misinterpreted as cardiac motion. The above false peaks are more apparent in certain combinations of the rotation and the data set than other combinations of the rotation and the data set.

Figure 8:
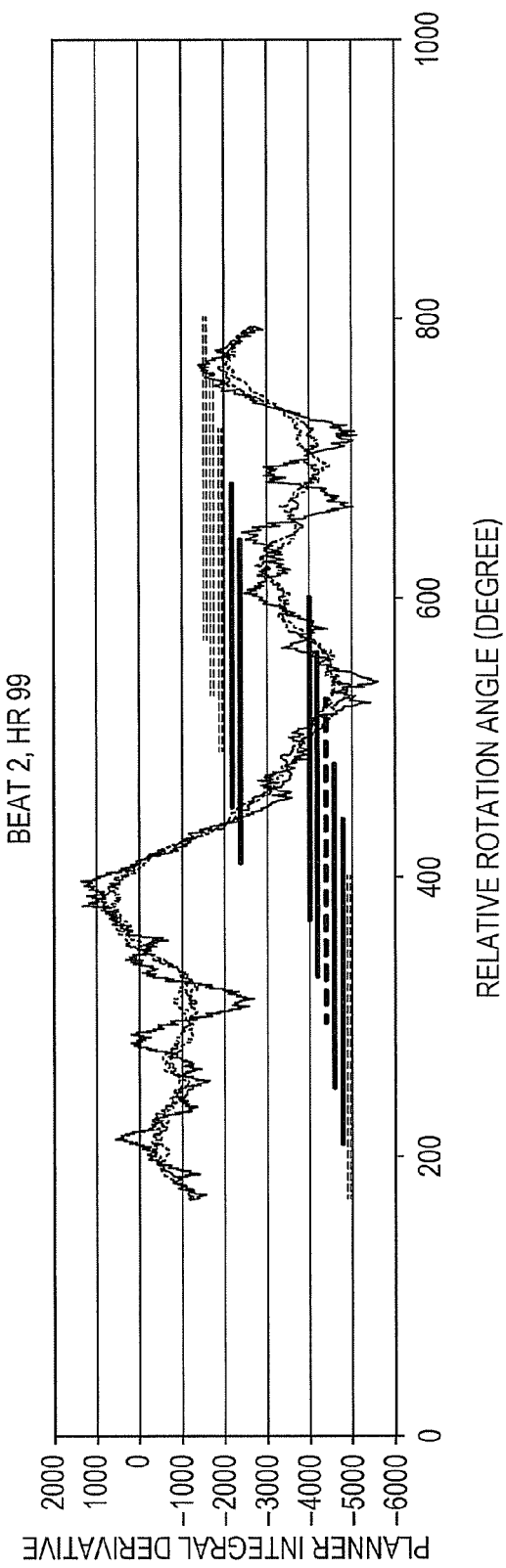
FIG. 8 illustrates changes in DPI over the course of one heart beat.

FIG. 8 illustrates changes in DPI over the course of one heart beat. As already described with respect to FIG. 7, although there appears to be the similar periodic feature of the beam hardening effect, the DPI values quickly change in response to certain cardiac motions. Over the course of one heart beat in the illustrated graph, the data covers approximately 600 degrees of rotation in the x axis while the DPI values are plotted in the y axis. The three sets of data are shown in the same graph. Furthermore, the graph includes three types of horizontal bars, and each bar type indicates a half scan view range that is shifted by 100 views from its preceding range. A dotted double bar represents a view range involving a relatively small amount of cardiac motion while a solid bar or a thick dotted single bar indicates a relatively large amount of cardiac motion. In this example, the projection data sets involving the least amount of cardiac motion range from approximately 500 degrees to approximately 800 degrees except for a single half scan view ranging from approximately 200 degrees to approximately 400 degrees as indicated by green horizontal bars. Although a single half scan view as indicated by the thick dotted single bar involves a large amount of motion, it is not clear as to why the reconstructed image showed less image showed less motion artifacts.

Figure 9:
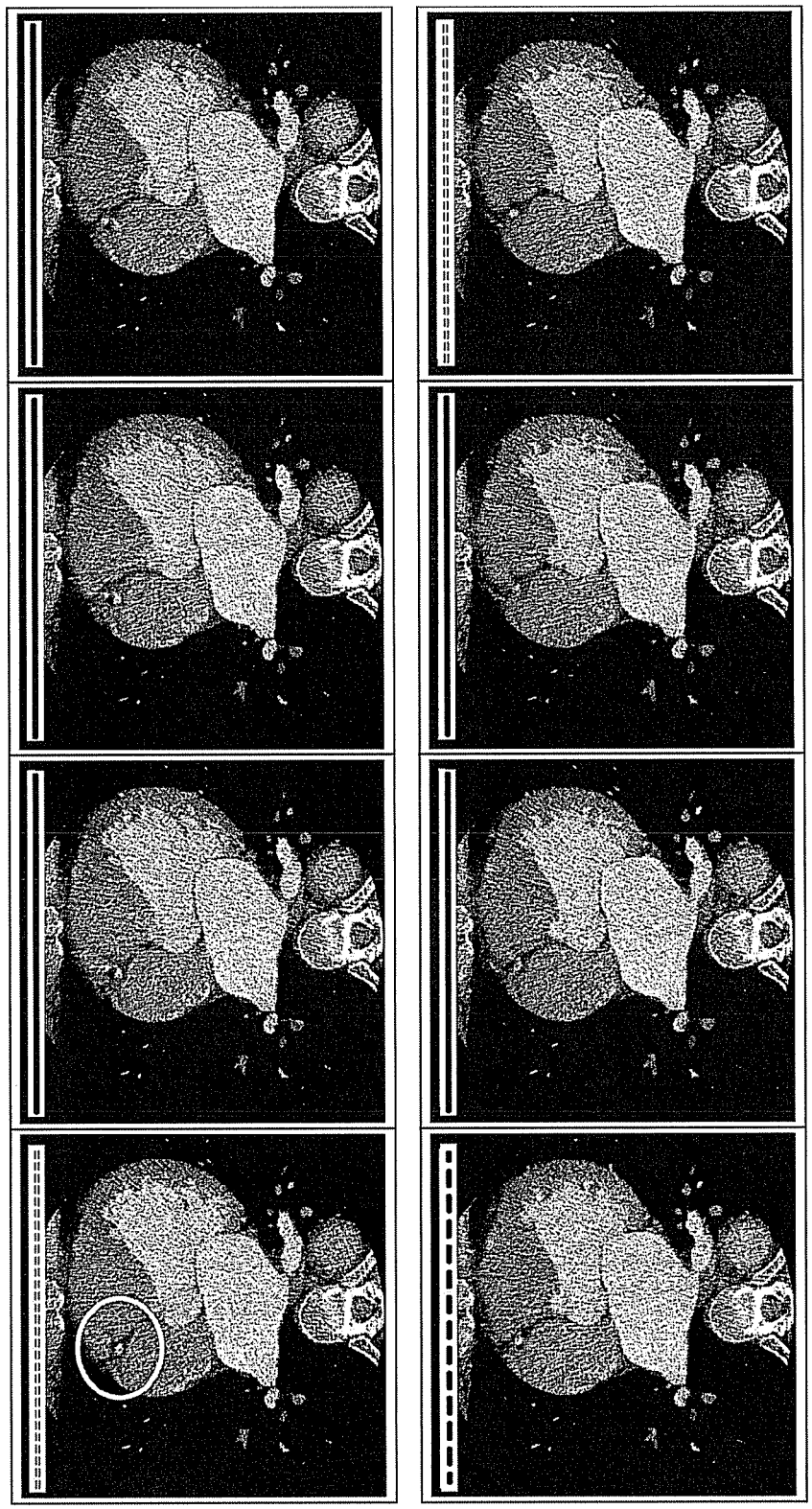
FIG. 9 illustrate the reconstructed images according to the selected half scan projection data of FIG. 8.

Now referring to FIG. 9, the reconstructed images are shown according to the selected half scan projection data of FIG. 8. The images with a dotted double bar have been reconstructed from the projection data in the dotted double half scan view range of FIG. 8. The dotted double half scan reconstructed images illustrate substantially no motion artifacts near the artery as indicated by a white circle in the top left image. On the other hand, the images with a solid bar have been reconstructed from the projection data in the solid half scan view range of FIG. 8. The solid half scan reconstructed images illustrate substantial motion artifacts near the same artery. Obviously, the motion artifacts near the artery are caused by the projection data that has been acquired during the presence of cardiac motion. An exception is the image with a dotted single bar. The images with a dotted single bar have been reconstructed from the projection data in the dotted single half scan view range of FIG. 8. The dotted single half scan reconstructed image illustrates substantially no motion artifacts near the same artery as indicated by the white circle in the top left reconstructed image. Although the data appears to be motion contaminated according to the DPI curve in FIG. 8, the image looks free of motion artifacts.

Figure 10:
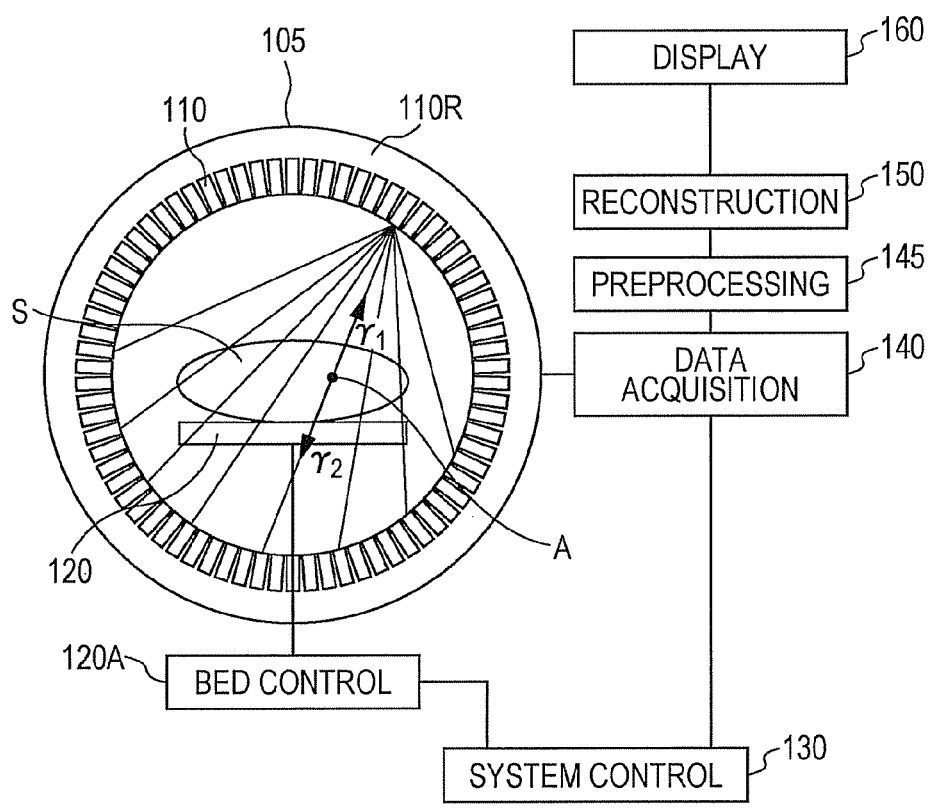
FIG. 10 is a diagram illustrating one embodiment of a positron emission tomography (PET) imaging system according to the present invention.

Now referring to FIG. 10, a diagram illustrating one embodiment of a positron emission tomography (PET) imaging system 100 according to the present invention. The emission data measurement system 100 includes a PET detector 105, which accommodates a two-dimensional array detector units 110. The two-dimensional array type detector units 110 are installed on a ring 110R around a subject S, who is laid on a sliding sheet bed 120. A bed controller 120A controls the sliding movement of the sliding bed 120 with respect to the detector units 110 in a perpendicular direction. The ring 110R is stationary while the sliding bed 120 moves along the central axis of the rings 110R at a predetermined speed or stationary during a data acquisition process.

A data acquisition unit 140 controls the detector units 110 in receiving the gamm photon data that are detected at the detector units 110. Unlike a CT system, the PET system 100 acquires the emission data rather than the projection data. That is, the PET imaging is based upon the gamma photon that is ultimately emitted inside the object of the interest due to the tracer isotope. Thus, a preprocessing unit 145 preprocesses the emission data before reconstruction by converting the emission data to projection data. Furthermore, the preprocessing unit 145 determines motion index values for the projection data using the derivatives of the planar integrals (DPI) according to the current invention. In addition, the preprocessing unit 145 selects projection data based upon the motion index values so that the selected projection data portions reflect a minimal amount of motion during the data acquisition. In turn, a reconstruction unit 150 reconstructs a set of desirable images based upon the selected projection data, and a display unit 160 display's the desirable images with a minimal amount of motion artifacts. A system control unit 130 in turn controls both the bed control unit 120A and the data acquisition unit 140. In the embodiment, emission data are collected in the following manner while the sliding bed 120 travels.

The PET system 100 operates in a manner that PET imaging is based upon the tracer concentration distribution. In this regard, before a PET scan, tracer radioisotope that emits positrons is injected into the patient body. The tracer is chemically incorporated into biologically active molecules such as fluorodeoxyglucose (FDG). After a waiting period during which the active molecules become concentrated in tissues of interest, the PET scanner 100 acquires raw data from the patient as the tracer decays. In further detail, during position emission decay, the radioisotope emits a positron that travels in tissue for a short distance as it loses kinetic energy until it interacts with an electron. Consequently, the positron annihilates and emits two gamma photons with energy of 511 keV in approximately 180 degrees apart in the opposite directions. Ultimately, the two photons can be coincidentally detected by the detector units 110.

Figure 11:
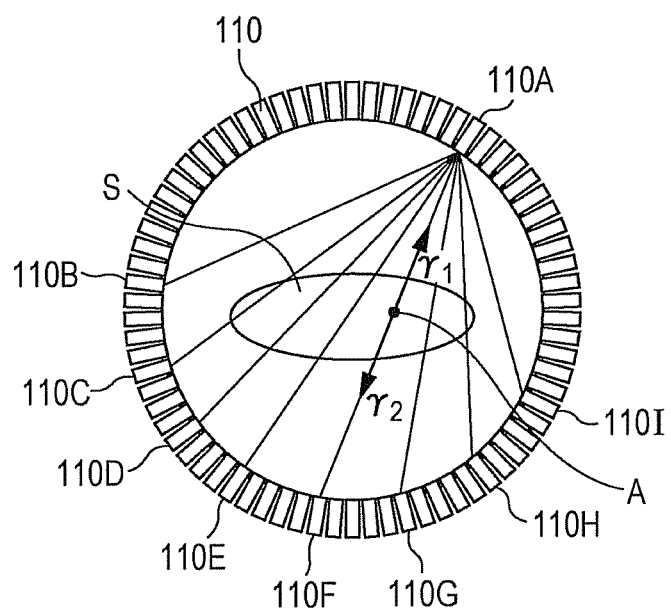
FIG. 11 is a diagram illustrating one embodiment of the PET detector.

Now referring to FIG. 11, the PET detector 100 consists of a number of detector rings 110R to cover a long subject such as a human. Each detector ring 110R is built by many units of gamma ray detectors 110 such as photomultiplier tubes or silicon avalanche photodiodes (Si APD). The raw data are collected by pairs of the detectors 110 and are a list of 'coincidence events' representing near-simultaneous detection of annihilation photons. That is, each coincidence event represents a line in space connecting the two detectors 110 along which the positron emission occurred. For example, from a certain point A in a subject S emits two photons along a direction of $\gamma_1$ towards a detector 110A and another direction of $\gamma_2$ towards a detector 110F. These two photons travel approximately 180 degrees with each other in the opposite directions as indicated by the two arrows. FIG. 11 also illustrates that other points in the same subject emit photons in substantially the same manner. That is, other pairs of the detectors such as 110A/110C, 110A/110D, 110A/110E, 110A/110G and 110A/110H also detect a list of 'coincidence events' representing near-simultaneous detection of annihilation photons. These emission data are preprocessed prior to a reconstruction process.

According to one embodiment of the preprocessing unit 145, the coincidence events are grouped into projection images such as sinograms based upon the angle of each view and tilt. In other words, the sinogram images are analogous to the projections captured by computed tomography (CT) scanners. Although the sonogram images are reconstructed in a similar way as CT, since a normal PET data set has millions of counts for the whole acquisition while the CT can reach a few billion counts, the PET data suffer from artifacts such as scatter and random events much more dramatically than the CT data. For the above reasons, a considerable amount of pre-processing is required for the PET data and includes correction for random coincidences, estimation and subtraction of scattered photons, detector dead-time correction and detector-sensitivity correction.

In addition, one embodiment of the preprocessing unit 145 selects a minimal motion portion of the projection data. The integrated coincidental signals are expressed in Equation (13) below, $$g(z,\phi;z',\phi') \approx \int dl a(\vec{x}) \exp[-\int dl' \mu(\vec{x})], \quad (13)$$

where $(z,\phi)$ and $(z',\phi')$ indicate the locations of the two detectors, $a(\vec{x})$ is the tracer concentration, and $\mu(\vec{x})$ represents the attenuation map. The integrals are along the line determined by the two detectors.

Assuming the attenuation map is known, the corrected data are expressed in Equation (14) below, $$g_c(z,\phi;z',\phi') = g(z,\phi;z',\phi') \exp[+\int dl' \mu(\vec{x})] = \int dl a(\vec{x}) \quad (14)$$

Fixing one detector unit, the corrected data are cone beam projections of the tracer concentration $a(\vec{x})$. The derivatives of the planar integral (DPI) of $a(\vec{x})$ are calculated from the corrected data $g_c(z,\phi;z',\phi')$. Based upon the DPI's, the embodiment of the preprocessing unit 145 selects a minimal motion portion of the projection data.

Figure 12:
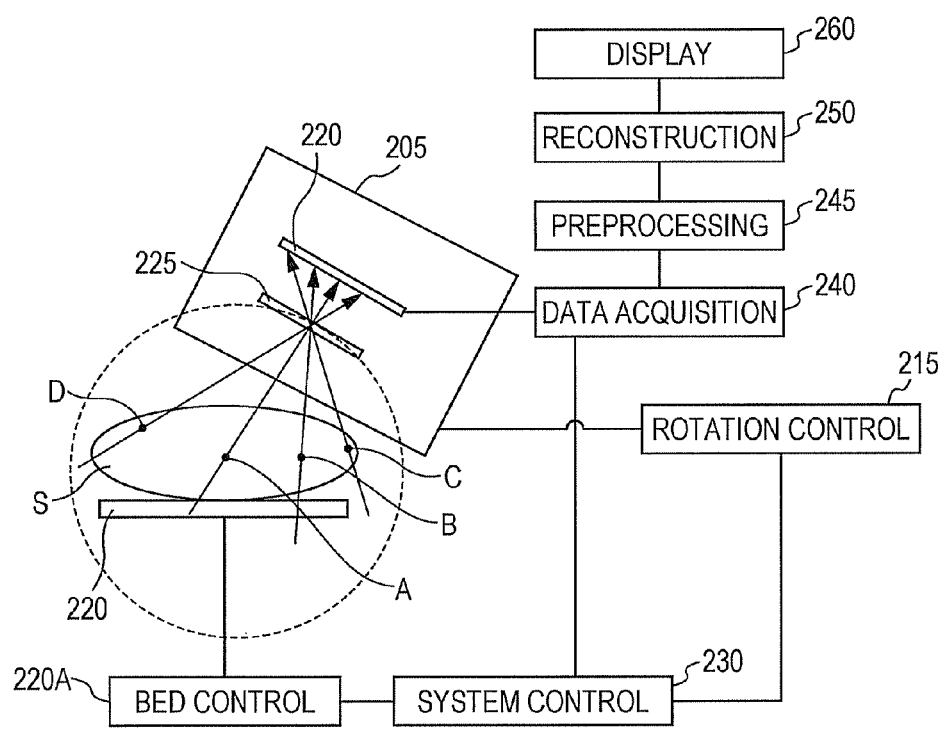
FIG. 12 is a diagram illustrating one embodiment of a single photon emission computed tomography (SPECT) imaging system according to the present invention.

Now referring to FIG. 12, a diagram illustrating one embodiment of a single photon emission computed tomography (SPECT) imaging system 200 according to the present invention. The emission data measurement system 200 includes at least one gamma ray detector 205 such as a gamma camera, which accommodates a two-dimensional array detector unit 210. The gamma ray detector 205 is placed over a subject S, who is laid on a sliding sheet bed 220. A rotational control unit 215 rotates the gamma ray detector 205 around the subject S as indicated by the dotted circle. A bed controller 220A controls the sliding movement of the sliding bed 120 with respect to the detector unit 205 in a perpendicular direction. The gamma ray detector 205 rotates around the subject S while the sliding bed 120 moves along the central axis of the rotation at a predetermined speed during a data acquisition process.

A data acquisition unit 240 controls the detector unit 205 in receiving the emission data that are detected at the detector units 220. Unlike a CT system, the SPECT system 200 acquires the gamma photon data rather than the projection data. That is, the SPECT imaging is based upon the gamma ray that is directly emitted inside the object of the interest due to the tracer isotope. Thus, a preprocessing unit 245 preprocesses the emission data before reconstruction by converting the emission data to projection data. Furthermore, the preprocessing unit 245 determines motion index values for the projection data using the derivatives of the planar integrals (DPI) according to the current invention. In addition, the preprocessing unit 245 selects projection data based upon the motion index values so that the selected projection data portions reflect a minimal amount of motion during the data acquisition. In turn, a reconstruction unit 250 reconstructs a set of desirable images from the selected projection data, and a display unit 260 displays the desirable images with a minimal amount of motion artifacts. A system control unit 230 in turn controls both the bed control unit 220A and the data acquisition unit 240. In the embodiment, emission data are collected in the following manner while the sliding bed 220 travels.

The SPECT system 200 operates in a manner that SPECT imaging is based upon the tracer concentration distribution.

In this regard, before a SPECT scan, tracer radioisotope that emits gamma radiation is injected into the patient body. The SPECT tracers are generally longer-lived more easily-obtained radioisotopes than the PET tracers. A marker radioisotope having its radioactive properties has been attached to a special radioligand having its chemical properties that is specifically binding to certain types of tissues. The SPECT scanner 200 acquires raw data from the patient as the tracer emits gamma radiation.

Figure 13:
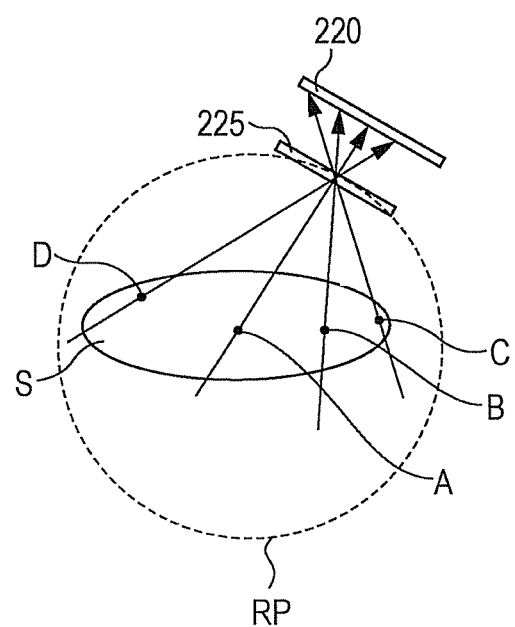
FIG. 13 is a diagram illustrating one embodiment of the SPECT detector.

Now referring to FIG. 13, the SPECT detector 220 directly measures gamma radiation emitted from a region of interest in the subject S. In the illustrated region of interest, four locations A, B, C and D emit gamma rays as indicated by the corresponding arrows. When the gamma camera 205 is located at a certain position on a rotational path RP as indicated by a dotted line, the two-dimensional detector 220 captures the raw data of the gamma rays that pass through a pinhole 225. That is, selected gamma rays are detected, and the data are acquired. For example, from a certain point A in a subject S emits gamma rays in different directions, but a gamma ray that travels through the pinhole 225 is recorded as indicated by the arrow. FIG. 13 also illustrates that other points in the same subject emit gamma rays and they are recorded in substantially the same manner as the gamma camera 205 rotates along the predetermined rotational path RP. These emission data are preprocessed prior to a reconstruction process.

According to one embodiment of the preprocessing unit 245, the gamma ray events are grouped into projection images such as sinograms based upon the angle of each view and tilt. In other words, the sinogram images are analogous to the projections captured by computed tomography (CT) scanners. As in the case of PET, a considerable amount of preprocessing is required for the SPECT data and includes correction for estimation and subtraction of scattered photons, detector dead-time correction and detector-sensitivity correction.

In one embodiment of the pinhole SPECT system 200, the measured signals on the 2D detector are expressed in Equation (15).

$$g(\vec{x}_0, u, v) \approx \int_0^\infty dt a(\vec{x}_0 + t\hat{e}) \exp[-\int_0^\infty dt' \mu(\vec{x}_0 + t\hat{e} + t'\hat{e})] \quad (15)$$

where $\vec{x}_0$ indicates the pinhole location; (u,v) is a point on the 2D detector; a(.) represents the tracer concentration; and $\mu$(.) is the attenuation map. Unit vector $\hat{e}$ is determined by the pinhole location $\vec{x}_0$ and the detector point (u,v). If the attenuation is ignored for the purpose of approximation, the projection data in a SPECT scan is expressed as in Equation (16), $$g(\vec{x}_0, u, v) \approx \int_0^\infty dt a(\vec{x}_0 + t\hat{e}) \quad (16)$$

Equation (16) is a cone beam transform of the tracer concentration. Thus, Grangeat's formula is used to obtain the derivatives of the planar integrals (DPI) of a(.) for the above described SPECT data. Based upon the DPI's, the embodiment of the preprocessing unit 245 selects a minimal motion portion of the projection data.

Figure 14:
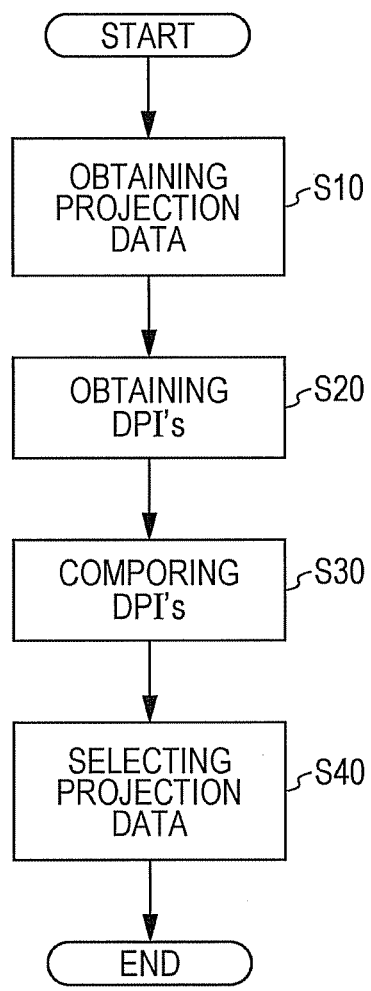
FIG. 14 is a flow chart illustrating steps involved in one preferred process of the current invention.

Now referring to FIG. 14, a flow chart illustrates steps involved in one preferred process according to the current invention. The process is optionally applicable using different modalities including but not limited to CT, PET and SPECT. In essence, the one embodiment of the process according to the current invention directly or indirectly obtains projection data and determines the derivatives of plane integral (DPI's) based upon the projection data. The embodied process then compares the DPI's for selecting a desirable portion of the projection data based upon the DPI comparison results. The embodied process finally reconstructs a desirable image based upon the selected portion of the projection data. The desirable image contains substantially minimal movement artifacts.

Still referring to FIG. 14, the embodied process ultimately selects a projection data portion for reconstructing images with substantially minimal movement artifacts. The embodied process initially obtains projection data for a region of interest in a subject in a step S10. For example, the projection data is directly obtained from an X-ray CT scanner.

In another example, the projection data is indirectly obtained from a PET scanner based upon the emission data. In a step S20, the derivatives of plane integrals (DPI's) are obtained from the projection data. For CT, the DPI is determined from projection data according to Equation (10). For PET, the derivatives of the planar integral of $a(\vec{x})$ are calculated from the corrected data as described in Equation (14). For SPECT, Grangeat's formula is used to obtain the derivatives of the planar integrals of a(.) from the SPECT data as described in Equation (16). In a step S30, the DPI's are compared to deteiffline an amount of movement of the region of interest based upon the difference between the DPI's. That is, the smaller the difference, the less the region of interest has moved. In a step S40, a portion of the projection data is selected based upon the comparison result in the step S30 comparison result in the step S30 so that an imaging system ultimately reconstructs a desirable image with substantially minimal movement artifacts.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

What is claimed is:

1. A method of determining a motion index in scanned data, comprising the steps of:
   obtaining raw data of an object at least from a first location and a second location using one device from a group of scanners involving CT, PET and SPECT;
   acquiring a first set of line integrals at the first location based upon a corresponding set of the raw data;
   acquiring a second set of line integrals at the second location based upon a corresponding set of the raw data;
   converting the first set of the line integrals and the second set of the line integrals to a derivative of a first plane integral (a first DPI) for a first plane and a derivative of a second plane integral (a second DPI) for a second plane, the first plane and the second plane being identical; and
   determining a first amount of motion of the object based upon a difference between the first DPI and the second DPI.

2. The method of determining a motion index in scanned data according to claim 1, further comprising additional steps of:
   using a CT scanner; and
   projecting onto the object x-ray from a source traveling over a predetermined trajectory including the first location and the second location.

3. The method of determining a motion index in scanned data according to claim 2 wherein the source uses a cone beam in said projecting step.

4. The method of determining a motion index in scanned data according to claim 3 wherein the first planar integral and the second planar integral are determined at a predetermined cone angle of the cone beam.

5. The method of determining a motion index in scanned data according to claim 4 wherein the cone angle is zero.

6. The method of determining a motion index in scanned data according to claim 1 wherein the first location and the second location are located on the predetermined trajectory at any angle with each other.

7. The method of determining a motion index in scanned data according to claim 1 wherein the first location and the second location are located on the predetermined trajectory at less than 180 degrees with each other.

8. The method of determining a motion index in scanned data according to claim 2 wherein the predetermined trajectory is circular.

9. The method of determining a motion index in scanned data according to claim 2 wherein the predetermined trajectory is helical.

10. The method of determining a motion index in scanned data according to claim 1 wherein the first set and the second set each include a predetermined number of consecutive views.

11. The method of determining a motion index in scanned data according to claim 1 wherein a plurality of the DPI's is used to analyze direction-dependent movements for a plurality of planes.

12. The method of determining a motion index in scanned data according to claim 1, further comprising the additional steps of:
    projecting onto the object x-ray from a source traveling over a predetermined trajectory including the first location and the second location;
    acquiring a third set of line integrals at the first location based upon a corresponding set of projection data;
    acquiring a fourth set of line integrals at the second location based upon a corresponding set of projection data;
    converting the third set of the line integrals and the fourth set of the line integrals respectively to a derivative of a third plane integral (a third DPI) for a third plane and a derivative of a fourth plane integral (a fourth DPI) for a fourth plane, the third plane and the fourth plane being identical; and
    determining a second amount of motion of the object along the third plane or the fourth plane based upon a difference between the third DPI and the fourth DPI.

13. The method of determining a motion index in scanned data according to claim 12 wherein the first amount of motion and the second amount of motion determine a direction-dependent movement of the object.

14. The method of determining a motion index in scanned data according to claim 13 wherein a minimal amount of the motion is selected.

15. The method of determining a motion index in scanned data according to claim 1 wherein the amount of the motion is compared to a predetermined value.

16. The method of determining a motion index in scanned data according to claim 1, comprising the additional steps of:
    using a PET scanner, the raw data being gamma photon data;
    obtaining at the first location first gamma photon data from a predetermined position in the object; and obtaining at the second location second gamma photon data from the predetermined position in the object, the second location being approximately 180 degrees apart from the first location.

17. The method of determining a motion index in scanned data according to claim 1, comprising the additional steps of:
  using a SPECT scanner, the raw data being gamma ray data;
  obtaining at the first location first gamma ray data from the object; and
  obtaining at the second location second gamma ray data from the object.

18. A system for determining a motion index in scanned data, comprising:
  a data acquisition unit for obtaining raw data of an object at least from a first location and a second location using one device from a group of scanners involving CT, PET and SPECT, said data acquisition unit acquiring a first set of line integrals at the first location based upon a corresponding set of the raw data and acquiring a second set of line integrals at the second location based upon a corresponding set of the raw data; and
  a processing unit connected to said data acquisition unit for converting the first set of the line integrals and the second set of the line integrals to a derivative of a first plane integral (a first DPI) for a first plane and a derivative of a second plane integral (a second DPI) for a second plane, the first plane and the second plane being identical, said processing unit determining an amount of motion of the object based upon a difference between the first DPI and the second DPI.

19. The system for determining a motion index in scanned data according to claim 18 wherein said device is a CT scanner and further comprising:
  a source unit located across from said data acquisition unit for projecting onto an object x-ray and traveling over a predetermined trajectory including the first location and the second location.

20. The system for determining a motion index in scanned data according to claim 19 wherein said source unit projects a cone beam.

21. The system for determining a motion index in scanned data according to claim 20 wherein the first planar integral and the second planar integral are determined at a predetermined cone angle of the cone beam.

22. The system for determining a motion index in scanned data according to claim 21 wherein the cone angle is zero.

23. The system for determining a motion index in scanned data according to claim 18 wherein the first location and the second location are located on the predetermined trajectory at any angle with each other.

24. The system for determining a motion index in scanned data according to claim 18 wherein the first location and the second location are located on the predetermined trajectory at less than 180 degrees with each other.

25. The system for determining a motion index in scanned data according to claim 19 wherein the predetermined trajectory is circular.

26. The system for determining a motion index in scanned data according to claim 19 wherein the predetermined trajectory is helical.

27. The system for determining a motion index in scanned data according to claim 18 wherein the first set and the second set each include a predetermined number of consecutive views.

28. The system for determining a motion index in scanned data according to claim 18 wherein a plurality of the DPI's is used to analyze direction-dependent movements for a plurality of planes.

29. The system for determining a motion index in scanned data according to claim 18, wherein said device is a CT scanner and further comprising:
  a source unit located across from said data acquisition unit for projecting onto the object x-ray and traveling over a predetermined trajectory including the first location and the second location, said data acquisition unit located across from said source unit for acquiring a third set of line integrals at the first location and a fourth set of line integrals at the second location, wherein said processing unit converts the third set of the line integrals and the fourth set of the line integrals into a derivative of a third plane integral (a third DPI) for a third plane and a derivative of a fourth plane integral (a fourth DPI) for a fourth plane, the third plane and the fourth plane being identical, said processing unit determining a second amount of motion of the object along the third plane or the fourth plane based upon a difference between the third DPI and the fourth DPI.

30. The system for determining a motion index in scanned data according to claim 29 wherein the first amount of motion and the second amount of motion determine a direction-dependent movement of the object.

31. The system for determining a motion index in scanned data according to claim 18 wherein a minimal amount of the motion is selected.

32. The system for determining a motion index in scanned data according to claim 18 wherein the amount of the motion is compared to a predetermined value.

33. The system for determining a motion index in scanned data according to claim 18, wherein said device is a PET scanner and the raw data is gamma photon data, said data acquisition unit obtaining at the first location first gamma photon data from a predetermined position in the object, said data acquisition unit obtaining at the second location second gamma photon data from the predetermined position in the object, the second location being approximately 180 degrees apart from the first location.

34. The system for determining a motion index in scanned data according to claim 18, wherein said device is a SPECT scanner and the raw data is gamma ray data, said data acquisition unit obtaining at the first location first gamma ray data from a predetermined position in the object, said data acquisition unit obtaining at the second location second gamma ray data from the predetermined position in the object.

* * * * *